(12) United States Patent
Nagesh et al.

(10) Patent No.: US 10,595,388 B2
(45) Date of Patent: Mar. 17, 2020

(54) CLOUD-BASED SYSTEMS AND METHODS FOR X-RAY TUBE AND GENERATOR CONFIGURATION MANAGEMENT

(71) Applicant: General Electric Company, Schenectady, NY (US)

(72) Inventors: Shivaprasad Nagesh, Bangalore (IN); Aniruddha Tiru, Bangalore (IN)

(73) Assignee: General Electric Company, Schenectady, NY (US)

( * ) Notice: Subject to any disclaimer, the term of this patent is extended or adjusted under 35 U.S.C. 154(b) by 321 days.

(21) Appl. No.: 15/718,815

(22) Filed: Sep. 28, 2017

(65) Prior Publication Data

US 2019/0098737 A1    Mar. 28, 2019

(51) Int. Cl.
| | | |
|---|---|---|
| H04L 29/06 | (2006.01) | |
| A61B 6/10 | (2006.01) | |
| H05G 1/54 | (2006.01) | |
| A61B 6/00 | (2006.01) | |

(52) U.S. Cl.
CPC .............. *H05G 1/54* (2013.01); *A61B 6/10* (2013.01); *A61B 6/40* (2013.01); *A61B 6/548* (2013.01); *A61B 6/56* (2013.01); *H04L 63/08* (2013.01); *H04L 63/1466* (2013.01); *H04L 63/0815* (2013.01); *H04L 63/123* (2013.01)

(58) Field of Classification Search
CPC .... H05K 1/0275; G06F 21/86; G08B 13/128; G07D 11/042; H05G 1/54; A61B 6/548; A61B 6/10; A61B 6/40; A61B 6/56; H04L 63/08; H04L 63/0815; H04L 63/123; H04L 63/1466
See application file for complete search history.

(56) References Cited

U.S. PATENT DOCUMENTS

| | | | | |
|---|---|---|---|---|
| 6,774,807 B1* | 8/2004 | Lehfeldt | .............. | G08B 29/046 324/110 |
| 7,692,421 B2* | 4/2010 | Veroni | ................. | G01R 22/066 324/110 |
| 2005/0120245 A1* | 6/2005 | Torisaki | .................. | G06F 21/64 726/4 |
| 2006/0101288 A1* | 5/2006 | Smeets | ................. | G06F 21/602 713/194 |
| 2008/0091605 A1* | 4/2008 | Hughes | .................. | G06F 21/31 705/51 |

(Continued)

*Primary Examiner* — Nelson S. Giddins
(74) *Attorney, Agent, or Firm* — Hanley, Flight and Zimmerman, LLC

(57) ABSTRACT

Methods and apparatus to prevent tampering with an x-ray tube are disclosed. An example circuit board device positioned with respect to the x-ray tube includes a processor and a memory. The example processor is to at least determine configuration information for the circuit board device. The example processor is to at least compare the determined configuration information to stored configuration information in the memory. The example processor is to at least, when the determined configuration information is verified with the stored configuration information, enable the circuit board device. The example processor is to at least, when the determined configuration information is not verified with the stored configuration information, i) disable the circuit board device and ii) process board reactivation before enabling the circuit board device.

16 Claims, 9 Drawing Sheets

(56) References Cited

U.S. PATENT DOCUMENTS

| | | | | |
|---|---|---|---|---|
| 2009/0129546 A1* | 5/2009 | Newman | A61B 6/4233 | 378/114 |
| 2009/0195394 A1* | 8/2009 | Johnson | G06F 21/554 | 340/584 |
| 2011/0227603 A1* | 9/2011 | Leon | H01L 23/576 | 326/8 |
| 2011/0244798 A1* | 10/2011 | Daigle | H04L 63/08 | 455/41.2 |
| 2012/0131673 A1* | 5/2012 | Caci | G06F 21/86 | 726/23 |
| 2013/0125204 A1* | 5/2013 | La Fever | G06F 21/44 | 726/2 |
| 2013/0259488 A1* | 10/2013 | Bernstein | H04B 10/85 | 398/140 |
| 2016/0180117 A1* | 6/2016 | Doyle | G01N 27/045 | 726/26 |
| 2017/0155512 A1* | 6/2017 | Ogura | H04L 9/32 | |
| 2018/0082818 A1* | 3/2018 | Meiler | H01J 35/025 | |
| 2018/0103923 A1* | 4/2018 | Meiler | A61B 6/58 | |
| 2018/0342360 A1* | 11/2018 | Hong | H01H 71/04 | |
| 2019/0313526 A1* | 10/2019 | Busby | H05K 1/181 | |

\* cited by examiner

CLOUD-BASED SYSTEMS AND METHODS FOR X-RAY TUBE AND GENERATOR CONFIGURATION MANAGEMENT

FIELD OF THE DISCLOSURE

This disclosure relates generally to x-ray configuration management, and, more particularly, to cloud-based methods, systems, and apparatus for x-ray tube and generator configuration management.

BACKGROUND

In non-invasive imaging systems, x-ray tubes are used in various x-ray systems and computed tomography (CT) systems as a source of ionizing (x-ray) radiation. The ionizing radiation is emitted from an x-ray tube in response to control signals during an examination or imaging sequence. An emitter within the cathode emits a stream of electrons in response to heat resulting from an applied electrical current, and/or an electric field resulting from an applied voltage to a properly shaped metallic plate in front of the emitter. The anode includes a target that is impacted by the stream of electrons. The target, as a result of impact by the electron beam, produces x-ray radiation to be emitted toward an imaged volume. In such imaging systems, a portion of the radiation passes through a subject of interest, such as a patient, baggage, or an article of manufacture, and impacts a digital detector or a photographic plate where the image data is collected. The signals are then processed to generate an image that may be displayed for review. Parts of the x-ray system, including the x-ray tube, deteriorate over time based on repeated use. Failure and/or other unacceptable degradation in use can occur unpredictably at inopportune times, resulting in a need to reobtain images and unnecessary x-ray exposure for patients, as well as wasted patient, radiologist, and x-ray technician time to arrange for a repeated scan. X-ray system downtime for repairs also negatively impacts healthcare facility scheduling, billing, and patient care. Additionally, unregulated, imitation, and/or other knock-off parts installed by untrained, unlicensed repair personnel pose a danger to x-ray system reliability, x-ray system accuracy, x-ray system function, and patient safety.

BRIEF SUMMARY

Certain examples provide a circuit board device positioned with respect to an x-ray tube to prevent tampering with the x-ray tube. The example circuit board device includes a processor and a memory. The example processor is to at least determine configuration information for the circuit board device. The example processor is to at least compare the determined configuration information to stored configuration information in the memory. The example processor is to at least, when the determined configuration information is verified with the stored configuration information, enable the circuit board device. The example processor is to at least, when the determined configuration information is not verified with the stored configuration information, i) disable the circuit board device and ii) process board reactivation before enabling the circuit board device.

Certain examples provide a tangible computer readable storage medium including instructions which, when executed, cause a processor to at least determine configuration information for a circuit board device associated with an x-ray tube. The example instructions, when executed, cause a processor to at least compare the determined configuration information to stored configuration information. The example instructions, when executed, cause a processor to at least, when the determined configuration information is verified with the stored configuration information, enable the circuit board device. The example instructions, when executed, cause a processor to at least, when the determined configuration information is not verified with the stored configuration information, i) disable the circuit board device and ii) process board reactivation before enabling the circuit board device.

Certain examples provide a method of preventing tampering with an x-ray tube. The example method includes determining, using a processor, configuration information for a circuit board device associated with the x-ray tube. The example method includes comparing, using the processor, the determined configuration information to stored configuration information in the memory. The example method includes, when the determined configuration information is verified with the stored configuration information, enabling the circuit board device. The example method includes, when the determined configuration information is not verified with the stored configuration information, i) disabling the circuit board device and ii) processing board reactivation before enabling the circuit board device.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

Figure 1:
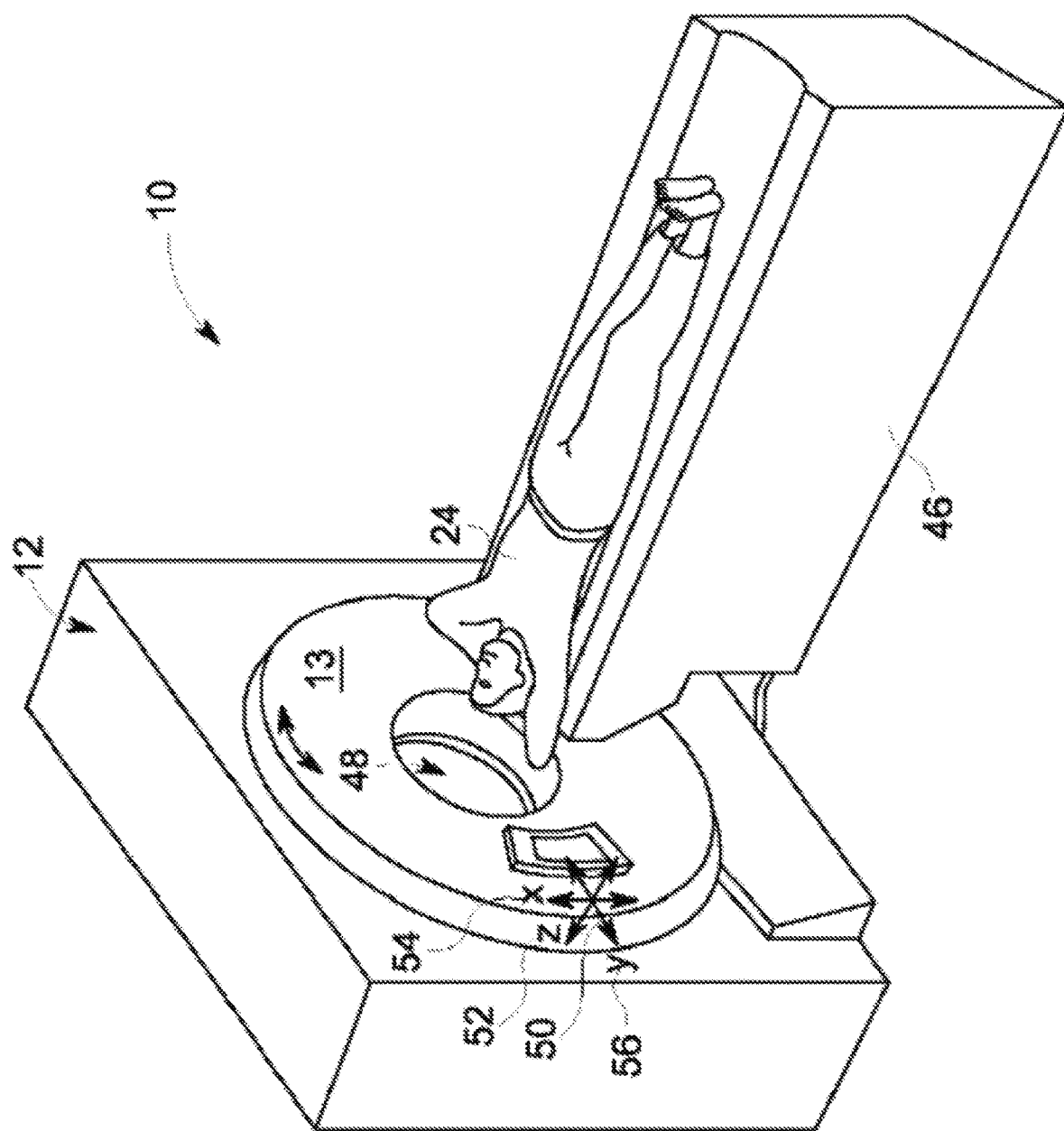
FIGS. 1-2 show an example computed tomography (CT) imaging system.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

Certain examples provide systems and methods to manage an integrity of system configuration of an x-ray tube and x-ray generator through cloud-based systems and methods deployed "in the field". In certain examples, a tamper detection board interacts with a cloud-based secure machine connectivity and access mechanism to enable access only to the authorized spare parts for the x-ray system. Configuration is managed online from the cloud which provides a secure system to store and control system configuration.

Tamper detection and/or prevention techniques typically involve erasing and/or damaging stored authentication keys when tampering is detected. Certain examples detect tampering used to corrupt stored keys. Certain examples provide a cloud based system to control configuration integrity of medical systems. Tamper detection/prevention helps to secure x-ray imaging devices and to ensure proper terms of use of deployed devices in the field, thus improving the quality of service provided to customers.

Certain examples leverage cloud and digital analytics to manage components of an x-ray system such as the x-ray tube, generator, etc., over a secured cloud channel. Certain examples use a smart processing board to detect tampering mounted on the x-ray tube casing. When powered up, the board checks the integrity of the data stored on the board's volatile memory. If the measured configuration is found to match the configuration in memory, then the board allows operation to proceed further. If the measured configuration is found not to match the configuration in memory, then the board sends an alert signal to the cloud while disabling further operation of the x-ray tube by sending a configuration mismatch message to the cloud-based monitoring system as well as to a system console. The disabled state can be overcome after a valid authorization is sent back to the board using the cloud system. A messaging protocol, such as MQ Telemetry Transport (MQTT), etc., can be used to send an activation instruction to the processing board. Once the board is reactivated, the board informs the cloud-based system indicating that a valid configuration has been found and allows further operation of x-tube and generator configuration.

In certain examples, a communication channel from which the configuration information is sent is a secured channel with user authentication, such as a single sign-on (SSO)-based access, etc. A secure communication channel helps ensure that only authorized personal can send an access key to a data lake, for example. Data can be fetched from the data lake by the processing board to be stored in the tamper detection board for further power cycles. Tamper protection board connectivity to the cloud is facilitated using a communication channel such as a Wi-Fi, Bluetooth Low Energy (BLE), or local area network (LAN) channel, in which the tamper detection board connects to a single board computer, which hosts a cloud-based engine, such as GE Predix®. Data received by the single board computer is sent to the data lake via the secured channel, for example.

At power-up, the single board processing computer receives the media access control identifier (MAC ID) of the tamper detection board. The MAC ID is sent to the central data lake to verify the authenticity or genuineness of the tamper detection board. If the tamper detection board is found to be genuine (e.g., a genuine spare), the single board processing computer allows further communication with the tamper detection board.

Thus, certain examples provide cloud-based configuration management to store and control system configuration via systems and methods to securely read, write and authenticate keys on the tamper detection board. When the system is initially installed and/or when authorized maintenance occurs, certain examples provide a method to securely manage the system configuration from a cloud based application with no human intervention. This maintains the integrity of the configuration management process, for example. The tamper detection board stores an activation key issued from the cloud during first installation, for example.

X-Ray tubes contain many proprietary designs that bring value in terms of imaging quality, life, reliability, etc. There are numerous attempts made in the field to reverse engineer x-ray tube configuration and replicate the same configuration with cheap and inferior substitutes. To protect proper x-ray tube configuration and, more importantly, to help ensure the x-ray tubes are used in the right way without tampering, systems and methods to detect and prevent unauthorized changes to x-Ray tubes. Cloud-based and secure communication channel links to x-ray tubes can be used to manage configuration to provide a robust configuration integrity management system for x-ray tubes and generators. An attempt to tamper with the x-ray system is detected and flagged and a provider and/or other maintainer is notified.

With authentic spares, a certain quality of performance can be guaranteed to a customer. This quality can be in question when spurious spares are used during maintenance. A configuration management and tamper protection system helps ensure that the guaranteed performance is maintained for the customer. An arrangement of tamper detection board combined with a cloud-based system offers a number of value propositions from genuine spare detection to new service models in which the x-ray tube and generator can be leased out for a prepaid time. Occasionally, spurious spares can also cause damage to other parts of the x-ray machine. Effective configuration management can also prevent damage due to cheap substitutes and help ensure guaranteed quality of service from medical devices on the field. Certain examples provide non-invasive and passive tamper detection methods to help ensure x-ray tube security even after months of storage and transportation. If the x-ray tube and/or generator has been tampered with, an alert can be generated and the component and/or x-ray system can be deactivated remotely from the cloud, for example.

In operation, for example, a sensor-enabled board configured on the x-ray tube detects tampering. Once the board detects the tamper, the board runs a cyclic redundancy check (CRC) internally (e.g., on every power up as well, etc.). When the CRC check does not match the stored or other reference value, a message is relayed to an edge device in communication with the cloud-based system. The edge device waits for authorization from the cloud before the edge device communicates with the board on the x-ray tube to restart operation. In certain examples, a message can be generated to notify support personnel that tampering has been identified and is being processed, for example.

Figure 2:
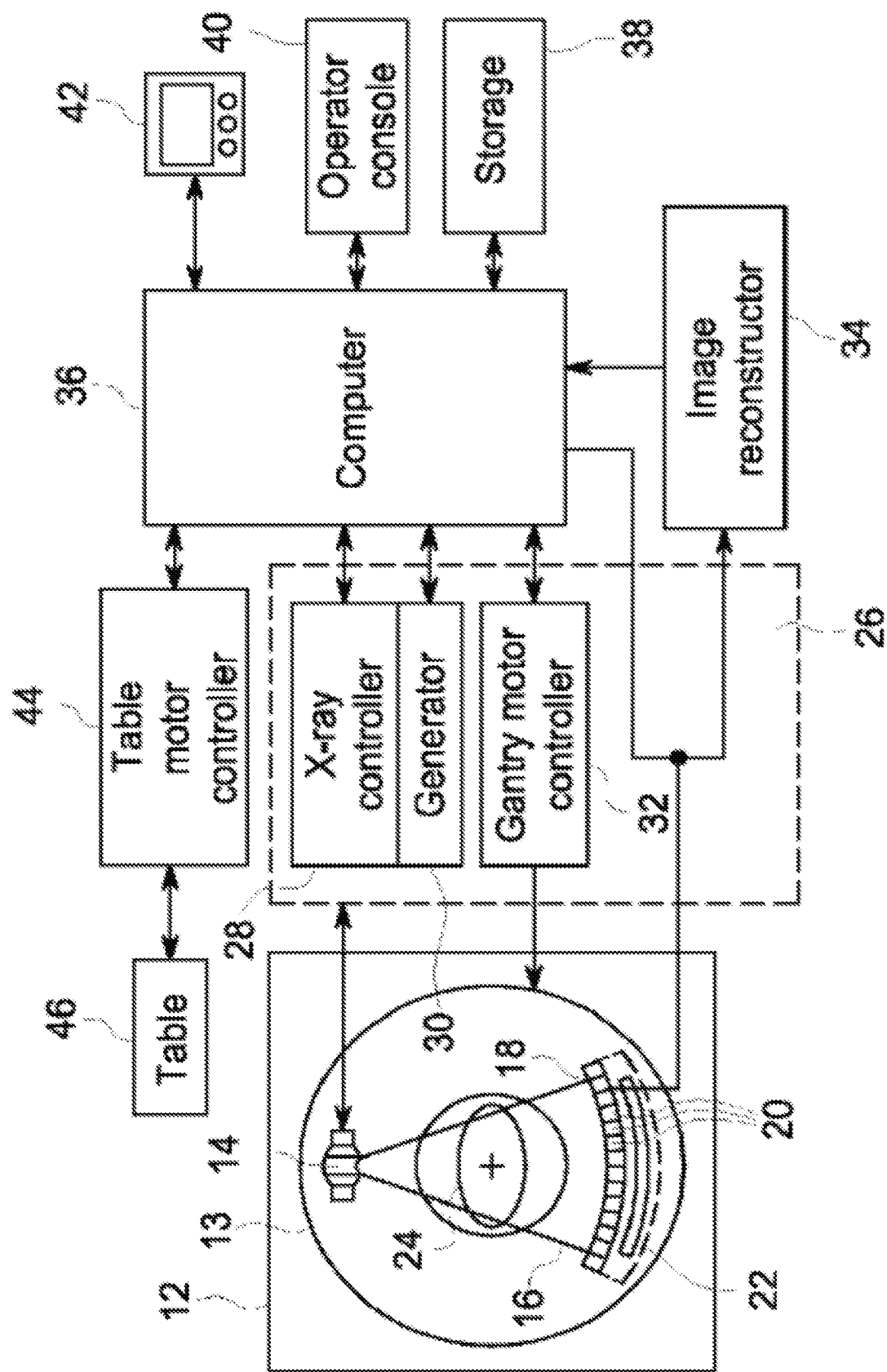

Turning to the figures, FIGS. 1 and 2 show a computed tomography (CT) imaging system 10 including a gantry 12. Gantry 12 has a rotary member 13 with an x-ray source 14 (e.g., an x-ray tube) that projects a beam of x-rays 16 toward a detector assembly 18 on the opposite side of the rotary member 13. A main bearing may be utilized to attach the rotary member 13 to the stationary structure of the gantry 12. The x-ray source 14 includes either a stationary target or a rotating target. The detector assembly 18 is formed by a plurality of detectors 20 and data acquisition systems (DAS) 22, and can include a collimator. The plurality of detectors 20 sense the projected x-rays that pass through a subject 24, and the DAS 22 converts the data to digital signals for subsequent processing. Each detector 20 produces an analog or digital electrical signal that represents the intensity of an impinging x-ray beam and hence the attenuated beam as it passes through a subject 24. During a scan to acquire x-ray projection data, the rotary member 13 and the components mounted thereon can rotate about a center of rotation.

Rotation of the rotary member 13 and operation of the x-ray source 14 are governed by a control mechanism 26 of the CT system 10. The control mechanism 26 can include an x-ray controller 28 and a generator 30 that provides power and timing signals to the x-ray source 14 and a gantry motor controller 32 that controls the rotational speed and position of the rotary member 13. An image reconstructor 34 receives sampled and digitized x-ray data from the DAS 22 and performs high speed image reconstruction. The reconstructed image is output to a computer 36 which stores the image in a computer storage device 38.

The computer 36 also receives commands and scanning parameters from an operator via an operator console 40 that has some form of operator interface, such as a keyboard, mouse, touch sensitive controller, voice activated controller, or any other suitable input apparatus. A display 42 allows the operator to observe the reconstructed image and other data from the computer 36. The operator supplied commands and parameters are used by the computer 36 to provide control signals and information to the DAS 22, the x-ray controller 28, and the gantry motor controller 32. In addition, the computer 36 operates a table motor controller 44 which controls a motorized table 46 to position the subject 24 and the gantry 12. Particularly, the table 46 moves a subject 24 through a gantry opening 48, or bore, in whole or in part. A coordinate system 50 defines a patient or Z-axis 52 along which the subject 24 is moved in and out of the opening 48, a gantry circumferential or X-axis 54 along which detector assembly 18 passes, and a Y-axis 56 that passes along a direction from a focal spot of the x-ray tube 14 to the detector assembly 18.

Figure 3:
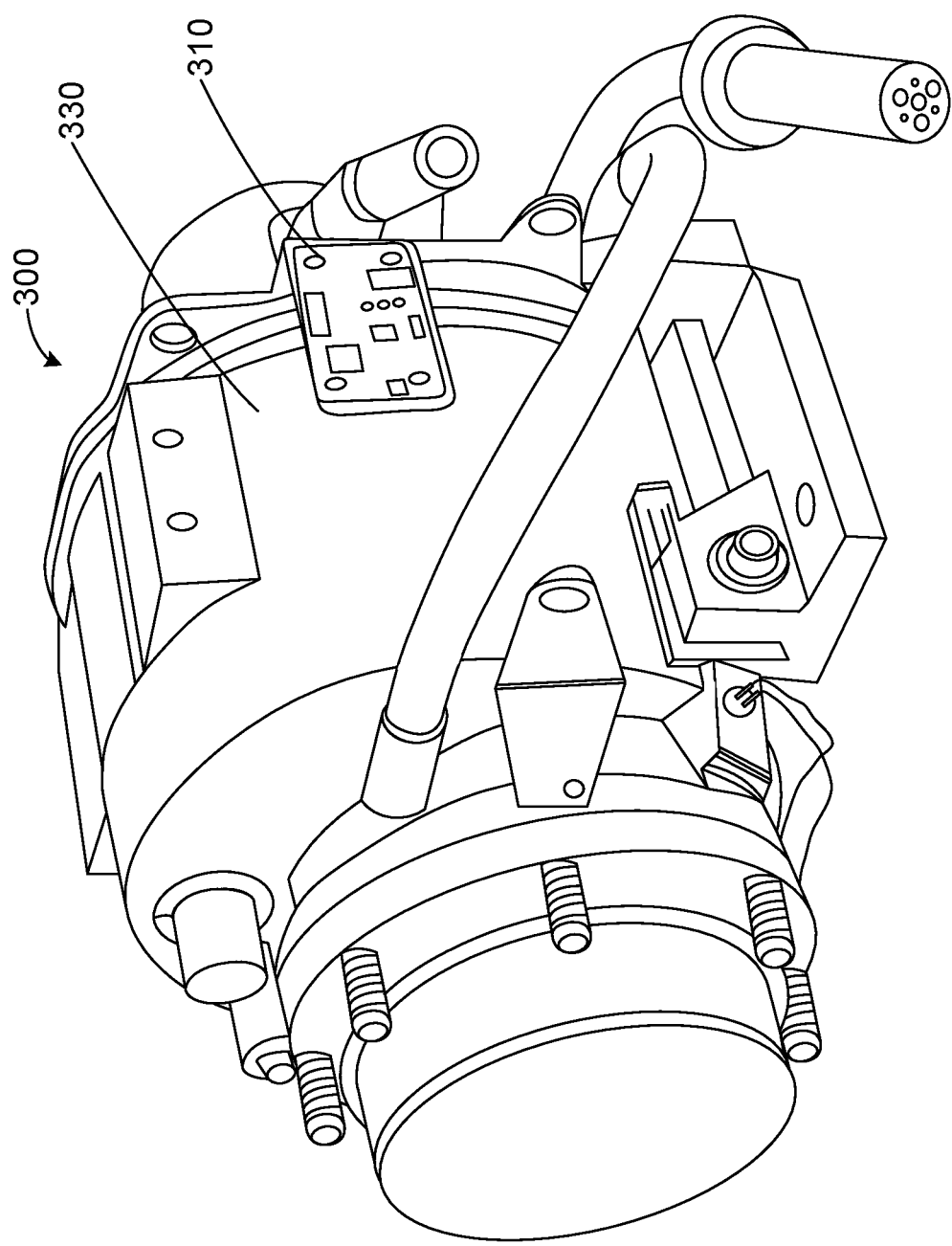
FIG. 3 illustrates an example x-ray tube that can form and/or be used in the x-ray source of the example of FIGS. 1-2.

FIG. 3 illustrates an example x-ray tube 300 that can form and/or be used in the x-ray source 14 of the example of FIGS. 1-2. The example x-ray tube 300 includes a tamper detection circuit board 310 mounted on a tube casing 330. The example tamper detection board 310 provides a secure machine connectivity and access mechanism to enable access to the x-ray tube 300 only for authorized spare parts, repair personnel, etc. Tamper detection and prevention is vital to secure proprietary intellectual property in the x-ray imaging device, as well as to help ensure proper terms of use with respect to a deployed x-ray device 300 in the field. Thus, quality of service can be maintained/improved.

Figure 4:
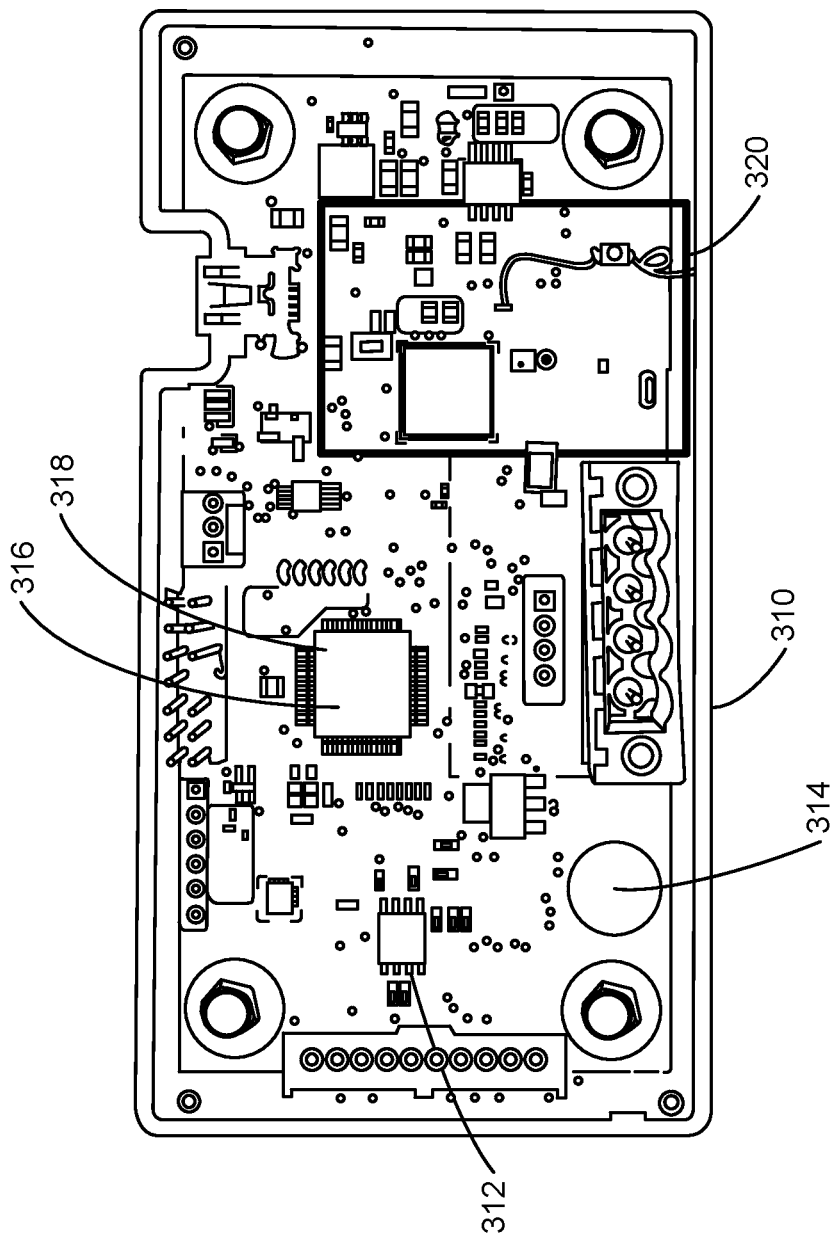
FIG. 4 illustrates an example implementation of the tamper detection circuit board.

FIG. 4 illustrates an example implementation of the tamper detection circuit board 310. In the example of FIG. 4, the board 310 includes passive electromagnetic circuitry embedded in the printed circuit board 310. By embedding the components into the board 310, the tamper detect mechanism is itself difficult to detect and bypass. The example implementation of the board 310 shown in FIG. 4 includes a magnetic actuated switch 312, and an energy storage device 314 (e.g., capacitor, supercapacitor, etc.), as well as a processor or controller 316, a memory 318 (e.g., a volatile and/or non-volatile memory, etc.), and a communication interface 320, such as for cloud connectivity via Wi-Fi, cellular, near field communication (NFC), and/or other wireless/wired communication interface. The processor 316 can include memory 318 such as volatile memory, non-volatile memory, etc., and/or the memory 318 can be on the board 310 separate from the processor 316. While the board 310 is mounted on the casing 330 of the x-ray tube 300, the magnetic switch 312 remains closed. However, if the board 310 is removed from the casing 330, the switch 312 opens and the board 310 is inactivated, disabling access to the x-ray tube 310 (e.g., physically and/or through data corruption, data loss, etc.). For example, opening the switch 312 cuts power to the memory 318 and configuration information, such as an activation or authorization key, etc., is wiped/erased/changed from the volatile memory 318.

Figure 5:
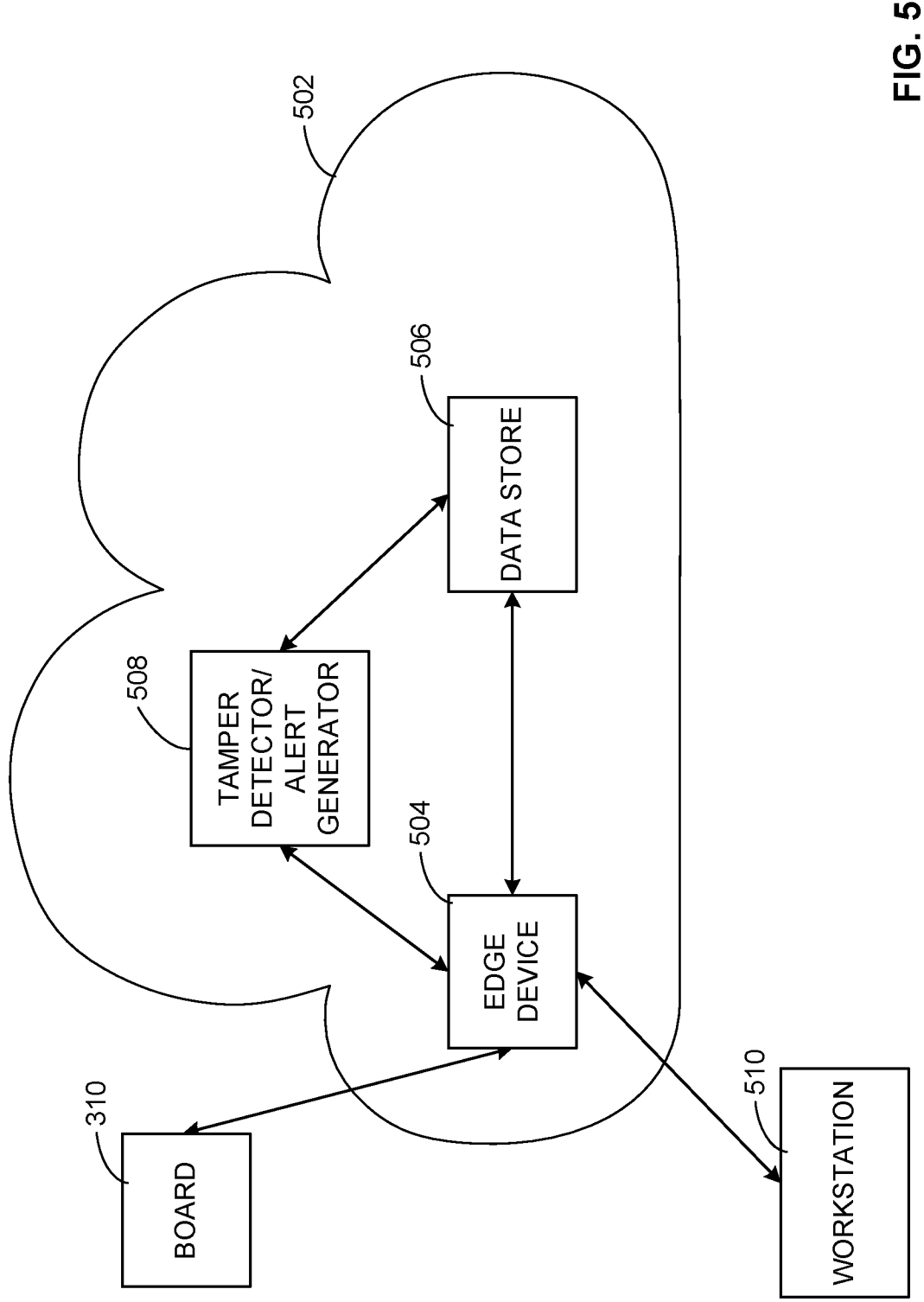
FIG. 5 illustrates an example implementation of a cloud infrastructure in communication with the tamper detection board.

FIG. 5 illustrates an example implementation of a cloud infrastructure 502 in communication with the tamper detection board 310. As shown in the example of FIG. 5, the board 310 communicates with an edge device 504 in and/or near the cloud 502, which facilitates exchange of data with respect to the cloud infrastructure 502. The edge device 504 provides information to a data store 506, for example. Thus, information from the board 310 can be provided to the cloud 502 and stored in the data store 506 for verification, analysis, authentication/authorization, etc. The cloud infrastructure 502 also includes a tamper detector/alert generator 508. The tamper detector/alert generator 508 can alert a user, system, application, and/or other device to tampering at the board 310, etc. In certain examples, the tamper detector/alert generator 508 can communicate with the board 310 to enable and/or disable access to the x-ray tube 300 based on determination or tampering or lack thereof, for example. Via a workstation 510, a user can view x-ray tube 300 and/or board 310 status and provide authentication and/or other command, control, query, feedback, etc., via an interface at the workstation 510, for example.

Figure 6:
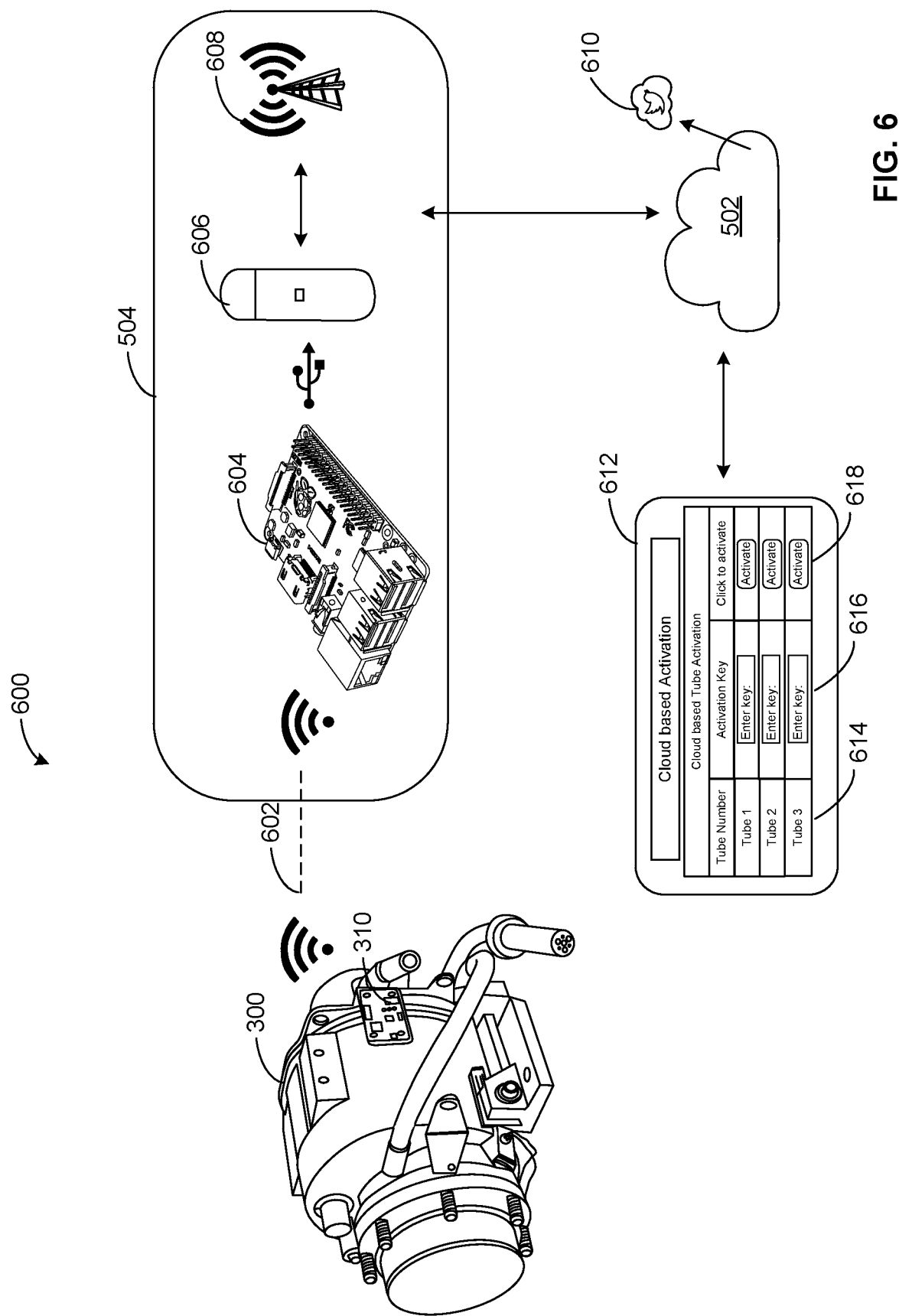
FIG. 6 illustrates an example monitoring ecosystem in which the x-ray tube and tamper detection board communicate via a wireless channel with the cloud infrastructure, directly and/or via the edge device.

FIG. 6 illustrates an example monitoring ecosystem 600 in which the x-ray tube 300 and tamper detection board 310 communicate via a wireless channel 602 (e.g., Wi-Fi, etc.) with the cloud infrastructure 502, directly and/or via the edge device 504. The example edge device 504 shown in FIG. 6 includes single board computer 604 (e.g., a Raspberry Pi, etc.) with a communication interface 606 (e.g. a 3G data card, etc.) providing access to a cellular network 608. Data gathered and processed via the cloud 502 to determine whether or not the board 310 and/or tube 300 has been tampered with can then be provided to one or more outputs such as the board 310, messaging/announcement 610, dashboard 612, etc.

As shown in the example of FIG. 6, x-ray tube 300 information can be provided to and displayed via the dashboard 612. The example dashboard 612 provides a list of identifier(s) 614 for available tube(s) 300 as well as a field for an activation key 616 for each tube 300 and a selection 618 to activate the corresponding tube 300. To activate a tube 300, a user locates the tube identifier 614 in the list and provides an activate key/code 616 for the tube 300. The user can then select to activate 618 that tube 300. Selecting to activate 618 the tube 300 triggers a verification of the activation key/code 616 via the cloud 502 (e.g., by the tamper detector/alert generator 508). If the activation key/code 616 is verified/validated, then an activation command/instruction is transmitted from the cloud 502 to the board 310 to enable the x-ray device 300.

In certain examples, the communication channel 602 is a secured channel with user authentication, such as a single sign-on (SSO)-based access, etc. The secure communication channel 602 helps ensure that only authorized personal can send an access key to and from the cloud 502, for example. Data can be fetched from the data store 506 in the cloud 502 via the edge device 504 to be stored in the tamper detection board 310 for further power cycles. Tamper protection board 310 connectivity to the cloud 502 is facilitated using the communication channel 602 such as a Wi-Fi, BLE, or LAN channel, in which the tamper detection board 310 connects to the edge device 504 (e.g., including the single board computer 604, etc.), which communicates with and/or hosts a cloud-based engine 508, such as GE Predix®. Data received by the single board computer 604 is sent to the data store 506 via the secured channel, for example.

At power-up, the single board processing computer 604 receives a media access control identifier (MAC ID) for the tamper detection board 310. The MAC ID is sent to the tamper detector/alert generator 508 to verify the authenticity or genuineness of the tamper detection board 310 via the data store 506 (e.g., a data lake, data warehouse, database, etc.) such as by verifying the MAC ID, performing a cyclic redundancy check, checksum, etc. If the tamper detection board 310 is found to be genuine (e.g., a genuine spare, untampered circuit board, etc.), the single board processing computer 604 allows further communication with the tamper detection board 310, for example.

When powered up, the tamper detection board 310 checks the integrity of the data stored on the board's volatile memory 318 (e.g., included with and/or separate from the processor 316, etc.). If the measured configuration determined by the processor 316 is found to match the configuration stored in memory 318, then the board 310 allows operation of the tube 300 (e.g., for operation, repair, replacement, configuration, update, etc.) to proceed. If the measured configuration is found not to match the configuration stored in memory 318, then the board 310 sends an alert signal to the cloud 502 (e.g., to the tamper detector/alert generator 508, etc.) and disables further operation of the x-ray tube 300 by sending a configuration mismatch message to the tamper detector/alert generator 508 of the cloud-based monitoring system 502. The disabled state can be overcome after a valid authorization is sent back to the board 310 using the cloud system 502 (e.g., by verifying the activation key 616 for the tube 300 via the dashboard 612 displayed at the workstation 510, etc.). A messaging protocol, such as MQ Telemetry Transport (MQTT), etc., can be used to send an activation instruction to the processing board 310. Once the board 310 is reactivated, the board 310 informs the cloud-based system 502 indicating that a valid configuration has been found.

While example implementations of the x-ray tube 14, 300 and associated components 502, 600 are illustrated in conjunction with FIGS. 1-6, processes and/or devices illustrated in conjunction with FIGS. 1-6 can be combined, divided, re-arranged, omitted, eliminated and/or implemented in any other way. Further, the example board 310, switch 312, energy storage device 314, processor 316, memory 318, communication interface 320, signal conditioning circuit 502, cloud infrastructure 502, edge device 504, data store 506, tamper detector/alert generator 508, workstation 510, single board computer 604, communication interface 606, etc., of FIGS. 1-6 can be implemented by hardware, machine readable instructions, software, firmware and/or any combination of hardware, machine readable instructions, software and/or firmware. Thus, for example, any of the example board 310, switch 312, energy storage device 314, processor 316, memory 318, communication interface 320, signal conditioning circuit 502, cloud infrastructure 502, edge device 504, data store 506, tamper detector/alert generator 508, workstation 510, single board computer 604, communication interface 606, etc., of FIGS. 1-6 can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example board 310, switch 312, energy storage device 314, processor 316, memory 318, communication interface 320, signal conditioning circuit 502, cloud infrastructure 502, edge device 504, data store 506, tamper detector/alert generator 508, workstation 510, single board computer 604, communication interface 606, etc., of FIGS. 1-6 is/are hereby expressly defined to include a tangible computer readable storage device or storage disk such as a memory, a digital versatile disk (DVD), a compact disk (CD), a Blu-ray disk, etc. storing the software and/or firmware. Further still, the example board 310 can include elements, processes and/or devices in addition to, or instead of, those illustrated in conjunction with FIGS. 1-6, and/or may include more than one of any or all of the illustrated elements, processes and devices.

Figure 7:
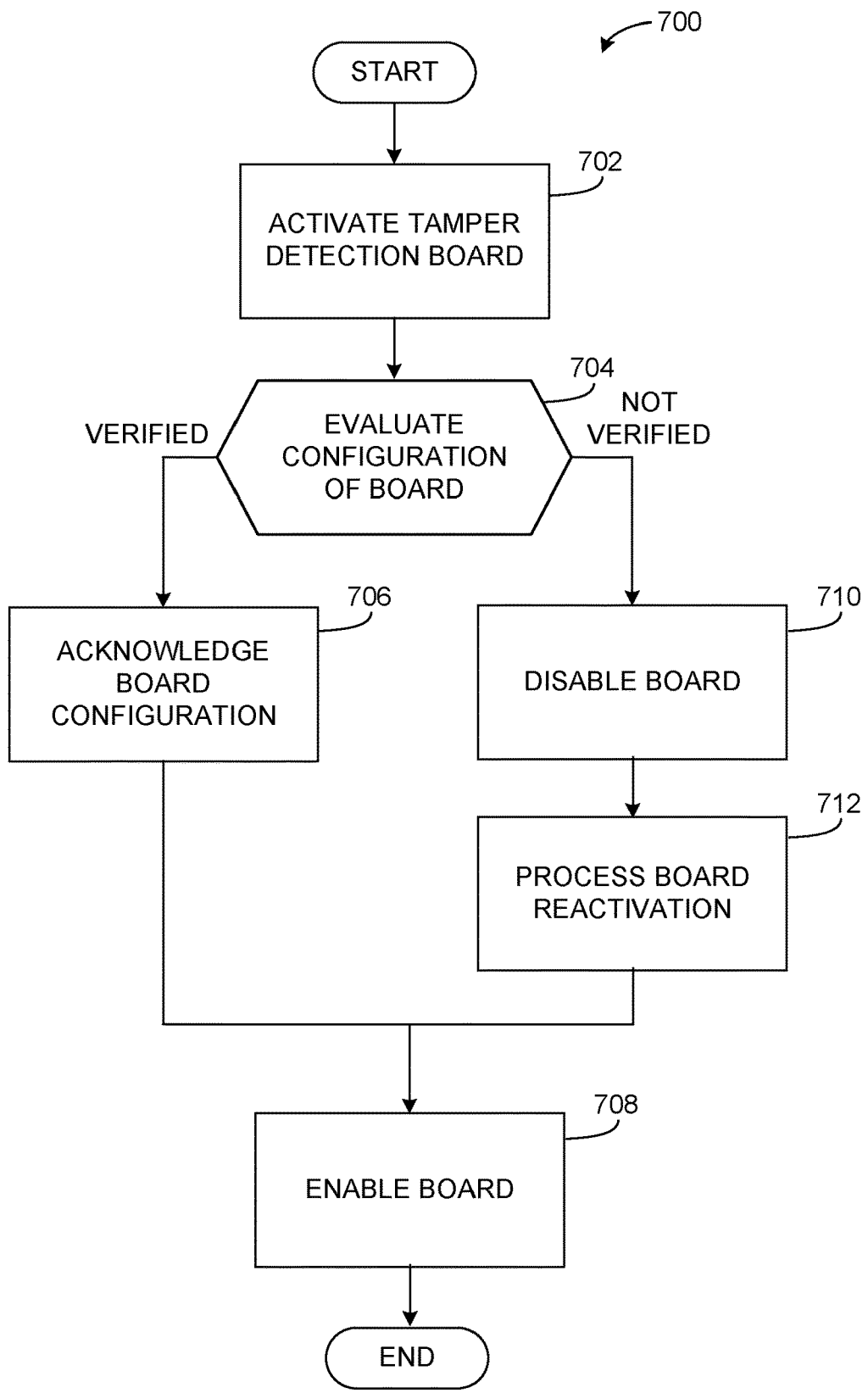
FIGS. 7-8 illustrate flow diagrams for example methods to detect and/or regulate tampering with an x-ray system.
Figure 8:
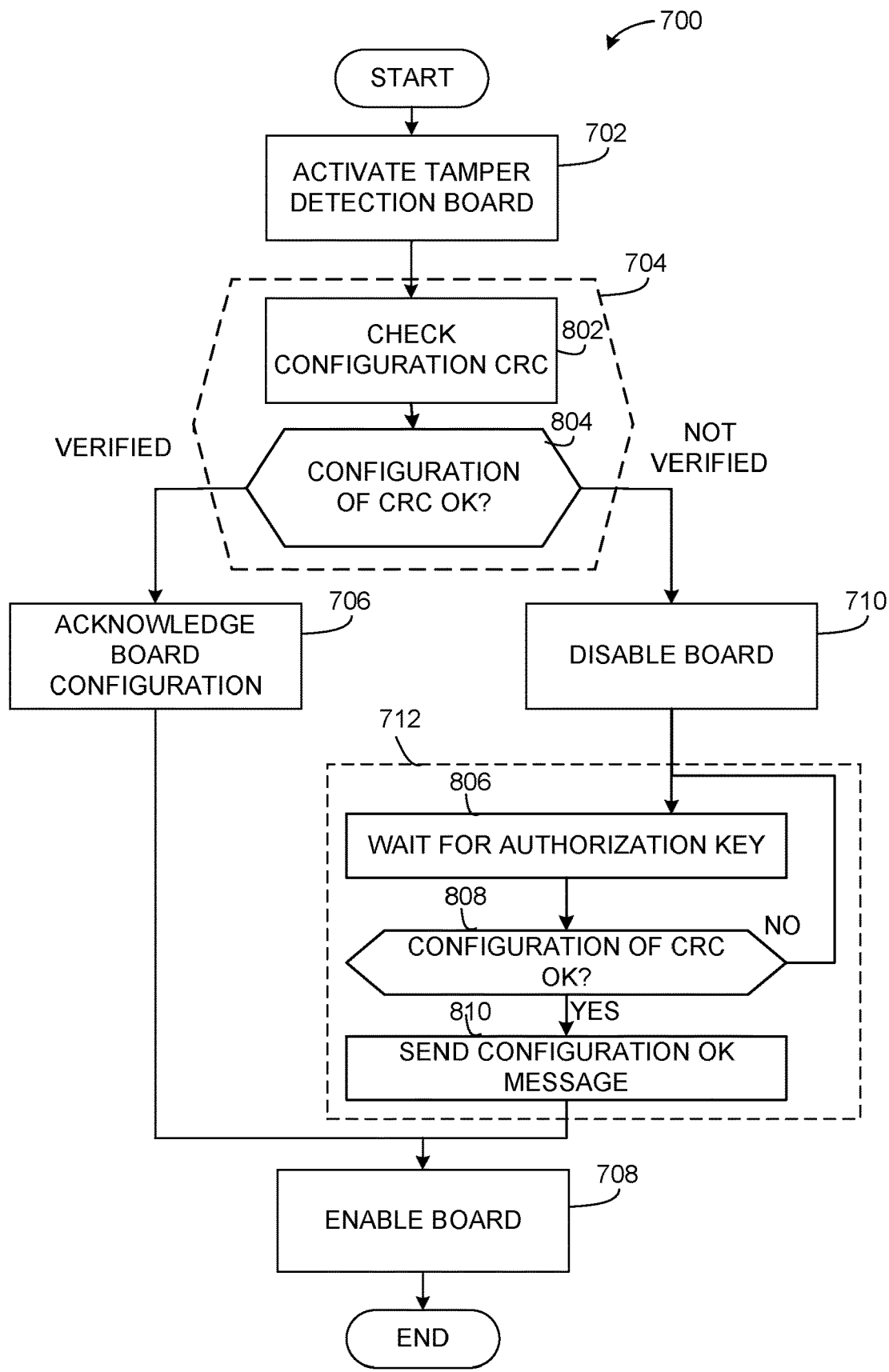

Flowcharts representative of example machine readable instructions for implementing and/or execution on the example tamper detection board 310 and/or cloud infrastructure 502, algorithms executing on or with respect to the example tamper detection board 310 and/or cloud infrastructure 502, and/or other components/processes of FIGS. 1-6 are shown in conjunction with FIGS. 7-8. Further, although the example program is described with reference to the flowcharts illustrated in conjunction with FIGS. 7-8, many other methods can alternatively be used. For example, the order of execution of the blocks may be changed, and/or some of the blocks described may be changed, eliminated, or combined. Although the flowcharts of FIGS. 7-8 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of FIGS. 7-8 an be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 7-8 an be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

FIG. 7 is a flow diagram of an example method 700 representative of example machine readable instructions that can be executed by the tamper detection board 310, cloud infrastructure 502, etc., to monitor and regulate tampering with the board 310 and/or the associated x-ray tube 300. At block 702, the tamper detection circuit board 310 is activated. For example, power is provided to the board 310, a button, switch, key, touchscreen, etc., is actuated, and/or other trigger such as attempted access to the x-ray tube 300 activates the board 310.

At block 704, the tamper detection circuit board 310 evaluates the configuration of the board 310 to determine whether or not the board 310 has been tampered with. For example, the tamper detection circuit board 310 determines configuration information associated with the board 310 and its x-ray tube 300. For example, the processor 316 of the tamper detection board 310 determines its MAC ID, other identification code, capacitance and/or magnetic field information, component configuration, etc. The tamper detection board 310 can compare the determined configuration information with stored configuration information to verify the determined configuration information. For example, the processor 316 compares the determined configuration information with stored configuration information saved in the memory 318, edge device 504, and/or data store 506, etc. The comparison can be computed using a CRC of the determined configuration information, such as an activation/authentication key, and the stored configuration information, such as an activation/authentication key, for example. Alternatively or in addition, the MAC ID of the board 310 can be verified. In certain examples, the edge device 504 facilitates verification in case the cloud 502 is disconnected from communication with the board 310, for example.

At block 706, if the determined configuration information is verified, then the board 310 configuration is acknowledged. At block 708, the board 310 and/or tube 300 is enabled. For example, the board 310 is enabled so that the x-ray tube 300 can be accessed for configuration, use, repair/replace, etc.

However, if the configuration information is not verified, then, at block 710, then the board 310 is disabled. For example, the tamper detection board 310 is locked, deactivated, and/or otherwise disabled to prevent access to and/or control of the x-ray tube 300. For example, an alert is sent to the tamper detector/alert generator 508 in the cloud 502 indicating possible tampering with the board 310 and/or other part of the tube 300, and the board 310 is notified that its configuration is not acceptable for use (e.g., has been tampered).

At block 712, reactivation of the board 310 is processed. For example, the board 310, edge device 504, and/or tamper detector/alert generator 508 await an authorization key, such as provided via the dashboard 612 on the workstation 510. Once the authorization key is provided, the configuration information is checked again to determine whether or not the board 310 is acceptable for use (e.g., no longer tampered, not in fact tampered, etc.). If the configuration information is not verified, then an updated/correct authentication key is awaited. If the configuration information can now be verified, then an acknowledgement and/or other authorization is provided to enable the board 310/tube 300 at block 708.

FIG. 8 is a flow diagram of an example implementation of the method 700 representative of example machine readable instructions that can be executed by the tamper detection board 310, cloud infrastructure 502, etc., to monitor and regulate tampering with the board 310 and/or the associated x-ray tube 300. At block 702, the tamper detection circuit board 310 is activated. For example, power is provided to the board 310, a button, switch, key, touchscreen, etc., is actuated, and/or other trigger such as attempted access to the x-ray tube 300 activates the board 310.

At block 704, the tamper detection circuit board 310 evaluates the configuration of the board 310 to determine whether or not the board 310 has been tampered with. For example, at block 802, a configuration CRC is performed on configuration information associated with the board 310 and its x-ray tube 300. For example, the processor 316 of the tamper detection board 310 determines and evaluates a CRC for the board 310 configuration, etc. At block 804, the CRC is evaluated to determine whether or not the board 310 has likely been tampered with. For example, the processor 316 compares the determined configuration information with stored configuration information saved in the memory 318, edge device 504, and/or data store 506, etc. The comparison can be computed using a CRC of the determined configuration information and the stored configuration information, for example. In certain examples, the edge device 504 facilitates verification in case the cloud 502 is disconnected from communication with the board 310, for example. If the CRC is verified, then control proceeds to block 706. If the CRC is not verified, then control proceeds to block 710.

At block 706, if the determined configuration information is verified, then the board 310 configuration is acknowledged. At block 708, the board 310 and/or tube 300 is enabled. For example, the board 310 is enabled so that the x-ray tube 300 can be accessed for configuration, use, repair/replace, etc.

However, if the configuration information is not verified, then, at block 710, then the board 310 is disabled. For example, the tamper detection board 310 is locked, deactivated, and/or otherwise disabled to prevent access to and/or control of the x-ray tube 300. For example, an alert is sent to the tamper detector/alert generator 508 in the cloud 502 indicating possible tampering with the board 310 and/or other part of the tube 300, and the board 310 is notified that its configuration is not acceptable for use (e.g., has been tampered).

At block 712, reactivation of the board 310 is processed. For example, at block 806, the board 310, edge device 504, and/or tamper detector/alert generator 508 await an authorization key, such as provided via the dashboard 612 on the workstation 510. Once the authorization key is provided, at block 808, the configuration information is checked again to determine whether or not the board 310 is acceptable for use (e.g., no longer tampered, not in fact tampered, etc.). If the configuration information is not verified, then an updated/correct authentication key is awaited. If the configuration information can now be verified, then, at block 810, an acknowledgement and/or other authorization is provided to enable the board 310/tube 300 at block 708.

Thus, from the foregoing, it is clear that certain examples provide a sensor-enabled circuit board 310 positioned on the x-ray tube 300 to detect tampering with the x-ray tube 300 and/or other x-ray system component. Once the board 310 detects tampering, the board 310 runs an internal CRC and/or other check (e.g., on power up as well as potential tamper detection, etc.). If the CRC does not match, then a message is relayed to the edge device 504. The edge device 504 withholds and authentication key and awaits authorization from the cloud 502 before the edge device 504 provides the authentication key to the board 310 to restart x-ray tube 300 operation, for example. A message can also be generated indicating/alerting to the potential and/or confirmed tampering, resumption of normal operation, request for repair, etc.

In certain examples, at power-up, the edge device 504 receives the MAC ID of the tamper detection board 310. The MAC ID is provided to the tamper detector/alert generator 508 to check the data store 506 to verify the genuineness of the board 310. If found to be genuine, further communication is permitted between the board 310 and the edge device 504. To be able to store and control system configuration for the x-ray tube 300, the board 310 should accept secure read, write, and authentication of one or more keys on the tamper detection board 310. When the system is initially installed and/or when authorized maintenance occurs, the system configuration can be securely managed via a cloud-based application 502 without human intervention while maintaining the integrity of configuration management processes, systems, etc.

The tamper detection board 310 stores an activation key issued from the cloud 502 during a first installation. The key written on volatile memory 318 can be generated using one or more secure algorithms, devices, etc. For example, a secure algorithm such as RSA, etc., can be used to generate and write the key. A combination of a plurality of keys such as board identifier, system identifier(s) for x-ray generator and tube(s) 300, a one-time passcode, etc., can be used to generate a key, for example. Key(s) can be passed on to a cloud based authentication manager 508, which hashes out another key to be stored on the volatile memory 318. When the system is reset or run, the generator checks for integrity of the key. If the key is corrupted, the generator stops the regular functioning of the X-Ray system and flags a warning that the configuration has been tampered with. During installation and in case of authorized maintenance activities, the authentication key can be regenerated as described above to restore functionality.

With authentic spares, a provider can and/or desires to guarantee a certain quality of performance to the customer. This quality can be in question when spurious spares are used during maintenance. The configuration management and tamper protection system 300, 600 helps ensure that the guaranteed performance is maintained for the customer. An arrangement of tamper detection board 310 combined with cloud 502 offers a plurality of value propositions from genuine spare detection to new service models in which the X-ray tube and generator can be leased out for a prepaid time. Occasionally, spurious spares can also cause damage to other parts of the X-Ray machine. Effective configuration management can thus also prevent damage due to cheap substitutes and ensure guaranteed quality of service from medical devices in the field. Other direct advantages include intellectual property (IP) protection, preventing unauthorized tampering and reconstruction by unauthorized agencies, etc. The commercial advantages come with protection of IP and with prevention of unauthorized maintenance and tampering by third parties. Technical advantages include the non-invasive and passive tamper detection methods. Hence, the tube 300 is secured even after months of storage and transportation against unauthorized use.

Figure 9:
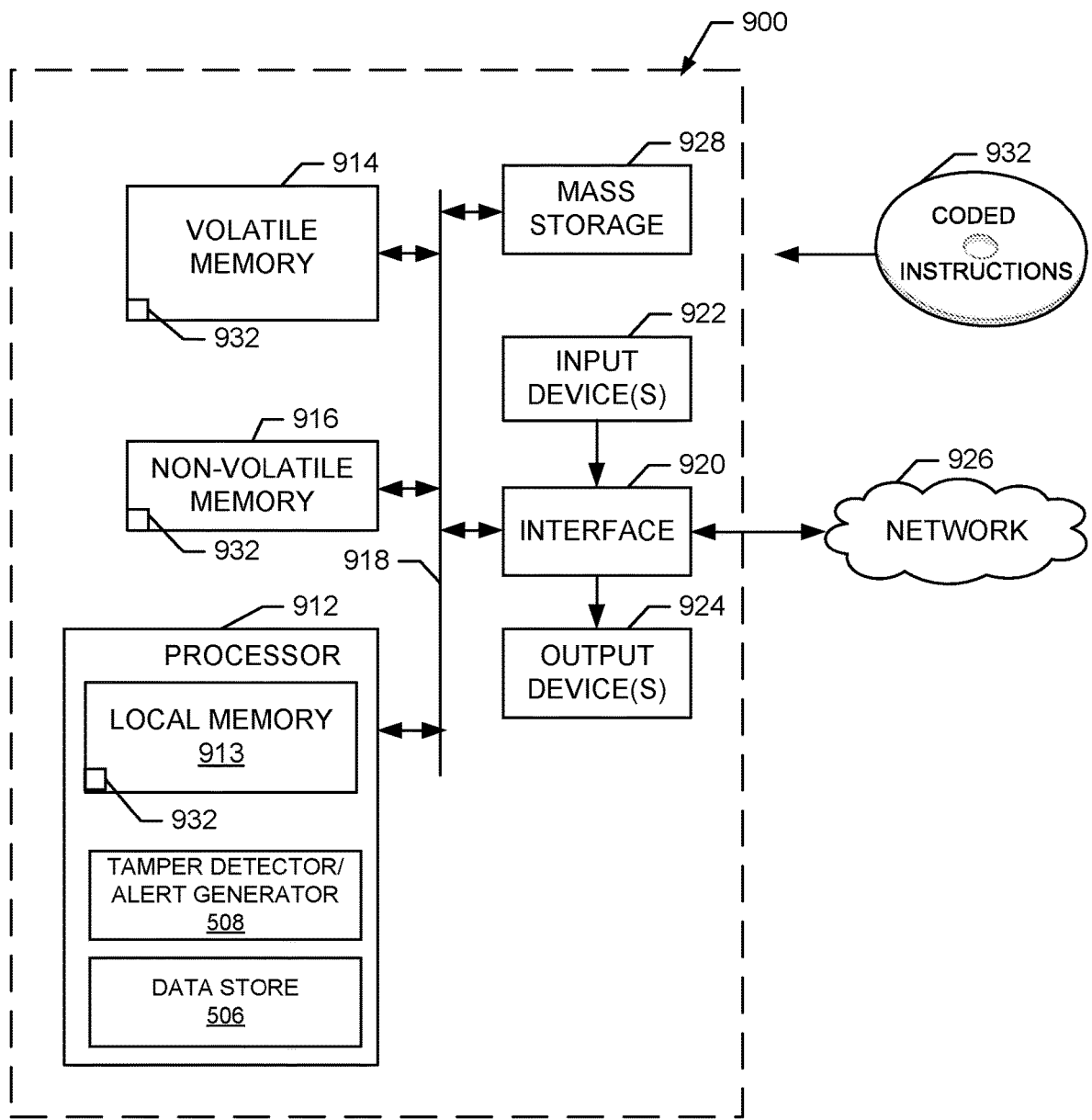
FIG. 9 is a block diagram of a processing system structured to execute the example machine readable instructions of FIGS. 7-8 to implement and/or interact with the example board and/or cloud infrastructure of FIGS. 1-6.

FIG. 9 is a block diagram of an example processor platform 900 structured to executing the instructions of FIG. 9 to implement the example board 310 and/or cloud infrastructure 502 of FIGS. 3-6. The processor platform 900 can be, for example, a server, a personal computer, a mobile device (e.g., a cell phone, a smart phone, a tablet such as an iPad™), a personal digital assistant (PDA), an Internet appliance, or any other type of computing device.

The processor platform 900 of the illustrated example includes a processor 912. The processor 912 of the illustrated example is hardware. For example, the processor 912 can be implemented by integrated circuits, logic circuits, microprocessors or controllers from any desired family or manufacturer.

In the examples, the machine readable instructions include a program for execution by one or more processors such as the processor 912 shown in the example processor platform 900 discussed below in connection with FIG. 9. The machine readable instructions may be stored on a tangible computer readable storage medium such as a CD-ROM, a floppy disk, a hard drive, a digital versatile disk (DVD), a Blu-ray disk, or a memory associated with the processor 912, but the entire program and/or parts thereof could alternatively be executed by a device other than the processor 912 and/or embodied in firmware or dedicated hardware.

The processor 912 of the illustrated example includes a local memory 913 (e.g., a cache). The example processor 912 of FIG. 9 executes the instructions of FIGS. 9-12 to implement the example board 310 and/or cloud infrastructure 504.

The processor 912 of the illustrated example is in communication with a main memory including a volatile memory 914 and a non-volatile memory 916 via a bus 918. The volatile memory 914 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 916 may be implemented by flash memory and/or any other desired type of memory device. Access to the main memory 914, 916 is controlled by a clock controller.

The processor platform 900 of the illustrated example also includes an interface circuit 920. The interface circuit 920 may be implemented by any type of interface standard, such as an Ethernet interface, a universal serial bus (USB), and/or a PCI express interface.

In the illustrated example of FIG. 9, one or more input devices 922 are connected to the interface circuit 920. The input device(s) 922 permit(s) a user to enter data and commands into the processor 912. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 924 are also connected to the interface circuit 920 of the illustrated example. The output devices 924 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 920 of the illustrated example, thus, typically includes a graphics driver card, a graphics driver chip or a graphics driver processor.

The interface circuit 920 of the illustrated example also includes a communication device such as a transmitter, a receiver, a transceiver, a modem and/or network interface card to facilitate exchange of data with external machines (e.g., computing devices of any kind) via a network 926 (e.g., an Ethernet connection, a digital subscriber line (DSL), a telephone line, coaxial cable, a cellular telephone system, etc.).

The processor platform 900 of the illustrated example also includes one or more mass storage devices 928 for storing software and/or data. Examples of such mass storage devices 928 include floppy disk drives, hard drive disks, compact disk drives, Blu-ray disk drives, RAID systems, and digital versatile disk (DVD) drives.

The coded instructions 932 of FIGS. 7-8 may be stored in the mass storage device 928, in the volatile memory 914, in the non-volatile memory 916, and/or on a removable tangible computer readable storage medium such as a CD or DVD.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A circuit board device positioned with respect to an x-ray tube to detect and prevent tampering with the x-ray tube, the circuit board device comprising:
   a processor and a memory,
   the processor to at least:
      determine configuration information for the circuit board device;
      compare the determined configuration information to stored configuration information in the memory;
      when the determined configuration information is verified with the stored configuration information, enable the circuit board device; and
      when the determined configuration information is not verified with the stored configuration information, i) disable the circuit board device and ii) process board reactivation before enabling the circuit board device, wherein processing the board reactivation includes verifying an activation key, the activation key to be transmitted to the circuit board device via a cloud infrastructure for comparison against a stored authorization key in the memory.

2. The circuit board device of claim 1, wherein the board reactivation is facilitated via an edge device in communication with the cloud infrastructure.

3. The circuit board device of claim 1, wherein the activation key is entered via a user interface and relayed to the circuit board device via the cloud infrastructure.

4. The circuit board device of claim 1, wherein the processor is to compare the determined configuration information to the stored configuration information using a cyclic redundancy check.

5. The circuit board device of claim 1, wherein the configuration information is determined based at least in part on a media access control identifier of the circuit board device.

6. The circuit board device of claim 1, wherein the circuit board device includes a magnetic switch that is opened when the circuit board device is removed from the x-ray tube, opening of the magnetic switch erasing the stored configuration information from the memory.

7. The circuit board device of claim 1, further including an energy storage device to retain configuration in the memory when external power is removed.

8. The circuit board device of claim 7, wherein disabling the circuit board device includes disrupting a memory configuration of the circuit board device when tampering is detected.

9. A tangible computer readable storage medium comprising instructions which, when executed, cause a processor to at least:
   determine configuration information for a circuit board device associated with an x-ray tube;
   compare the determined configuration information to stored configuration information;
   when the determined configuration information is verified with the stored configuration information, enable the circuit board device; and
   when the determined configuration information is not verified with the stored configuration information, i) disable the circuit board device and ii) process board reactivation before enabling the circuit board device, wherein processing the board reactivation includes verifying an activation key, the activation key transmitted to the circuit board device via a cloud infrastructure for comparison against a stored authorization key in memory.

10. The computer readable storage medium of claim 9, wherein the board reactivation is facilitated via an edge device in communication with the cloud infrastructure.

11. The computer readable storage medium of claim 9, wherein the activation key is entered via a user interface and relayed to the circuit board device via the cloud infrastructure.

12. The computer readable storage medium of claim 9, wherein the instructions, when executed, cause the processor to compare the determined configuration information to the stored configuration information using a cyclic redundancy check.

13. The computer readable storage medium of claim 9, wherein the configuration information is determined based at least in part on a media access control identifier of the circuit board device.

14. A method of preventing tampering with an x-ray tube, the method comprising:
   determining, using a processor, configuration information for a circuit board device associated with the x-ray tube;

comparing, using the processor, the determined configuration information to stored configuration information in the memory;

when the determined configuration information is verified with the stored configuration information, enabling the circuit board device; and when the determined configuration information is not verified with the stored configuration information, i) disabling the circuit board device and ii) processing board reactivation before enabling the circuit board device, wherein processing the board reactivation includes verifying an activation key, the activation key transmitted to the circuit board device via a cloud infrastructure for comparison against a stored authorization key in the memory.

15. The method of claim 14, wherein the board reactivation is facilitated via an edge device in communication with the cloud infrastructure.

16. The method of claim 14, wherein comparing further includes comparing the determined configuration information to the stored configuration information using a cyclic redundancy check.

* * * * *